US005302515A

United States Patent [19]

Goodwin, Jr.

[11] Patent Number: 5,302,515

[45] Date of Patent: Apr. 12, 1994

[54] CHEMOTACTIC TEST APPARATUS AND METHOD

[75] Inventor: Richard H. Goodwin, Jr., Bethesda, Md.

[73] Assignee: Neuro Probe, Inc., Cabin John, Md.

[21] Appl. No.: 932,976

[22] Filed: Aug. 20, 1992

[51] Int. Cl.[5] .......................... C12Q 1/02; C12M 3/04; C12M 1/18; C12M 1/20; B01L 11/00

[52] U.S. Cl. ...................................... 435/29; 435/285; 435/300; 435/301; 422/101

[58] Field of Search ................. 435/29, 285, 300, 301; 422/101

[56] References Cited

U.S. PATENT DOCUMENTS

| | | | |
|---|---|---|---|
| 3,888,770 | 6/1975 | Avital et al. | 210/238 |
| 3,929,583 | 12/1975 | Sharpe et al. | 435/301 |
| 4,317,726 | 3/1982 | Shepel | 210/236 |
| 4,493,815 | 1/1985 | Fernwood et al. | 422/101 |
| 4,514,495 | 4/1985 | Schalkowsky et al. | 435/32 |
| 4,714,674 | 12/1987 | Palladino | 435/18 |
| 4,912,057 | 3/1990 | Guirguis et al. | 435/285 |
| 5,023,173 | 6/1991 | Horwitz et al. | 435/29 |

OTHER PUBLICATIONS

S. H. Zigmond and D. A. Lauffenburger, "Assays of Leukocyte Chemotaxis," Annual Review of Medicine, 37, pp. 149–155.

B. Gatewood, J. Joe and S. H. Zigmond, "CD45 is not Involved in the Processing of Spatial Information Required for Chemotaxis," Journal of Immunology, vol. 147, pp. 243–246.

Falk, W., Goodwin, Jr., R. H. and Leonard, E. J., "A 48-Well Micro Chemotaxis Assembly for Rapid and Accurate Measurement of Leukocyte Migration," Journal of Immunological Methods, 33, 1980, pp. 239–247.

Falk, W., Harvath, L. and Leonard, E. J., "Only the Chemotactic Subpopulation of Human Blood Monocytes Expresses Receptors for the Chemotactic Peptide N-Formylmethionyl-Leucyl-Phenylalanine," Infection and Immunity, vol. 36, No. 2, May 1982, pp. 429–454.

Harvath, L., Falk, W. and Leonard, E. J., "Rapid Quantitation of Neutrophil Chemotaxis: Use of a Polyvinylpyrrolidone-Free Polycarbonate Membrane in a Multiwell Assembly," Journal of Immunological Methods, 37, 1980, pp. 39–45.

Harvath, L. and Leonard, E. J., "Two Neutrophil Populations in Human Blood with Different Chemotactic Activities: Separation and Chemoattractant Binding," Infection and Immunity, vol. 36, No. 2, May 1982, pp. 443–449.

Richard, K. L. and McCullough, J., "A Modified Microchamber Method for Chemotaxis and Chemokinesis," Immunological Communications, 13(1), 1984, pp. 49–62.

*Primary Examiner*—Douglas W. Robinson
*Assistant Examiner*—Jon P. Weber
*Attorney, Agent, or Firm*—Kirkland & Ellis

[57] ABSTRACT

The present invention is a single site or multiple site chemotaxis test apparatus or chemotaxis chamber for measuring the effect of concentration gradients of diffusible chemicals upon the directional response of biological cells. The chemotactic test apparatus of the present invention comprise two compartments separated by a thin passage. The dimensions of the thin passage are selected such that cells cannot flow through the thin passage, but must deform themselves by flattening out and then "crawl" or migrate through the passage. These chambers can be used to study the migration or orientation of mobile adherent or non-adherent cells.

32 Claims, 3 Drawing Sheets 18
14a 29a 25 13 29b 14b 11
10 16 17 12 20 28 27 19

CHEMOTACTIC TEST APPARATUS AND METHOD

BACKGROUND

1. Field of the Invention

The present invention relates to chemotaxis chambers, i.e., to chambers for measuring the effect of concentration gradients of diffusible chemicals upon the directional response of biological cells. More specifically, the present invention relates to chemotaxis chambers comprising two compartments separated by a thin passage, used to study the migration or orientation of adherent mobile cells.

2. Background of the Invention

Chemotaxis is the directional response of biological cells or organisms to concentration gradients of mobile chemicals. Conventional chemotaxis chambers comprise two compartments separated by a filter, with one or both of the compartments open to air. Cells in suspension are placed in the upper compartment, and a chemotactic factor or control is placed in the bottom compartment. The chemotactic factor can be used in various dilutions to get a dose-response curve. The controls are generally of two kinds: negative, when the same medium is used to suspend the cells above and below the filter; and chemokinetic, when a chemotactic factor is placed in the same concentration in the medium with the cells and on the opposite side of the filter. Chemokinetic controls allow the user to distinguish heightened random activity of the cells, due to contact with the chemotactic factor, from directional response in a concentration gradient of the chemotactic factor.

Chemotactic activity is measured by first establishing a stable concentration gradient in the chemotaxis chamber. The chamber is incubated for a predetermined time, then the filter is removed from the apparatus. The cells that have migrated through the filter (or into the filter to a certain depth) are then counted. A comparison is then made between the activity of the cells in a concentration gradient of the chemotactic factor being tested, and the activity of the cells in the absence of the concentration gradient.

The apparatus can also be used to measure the response of cells of different origins—e.g., immune cells from patients suffering from diseases—to a chemotactic factor of known chemotactic activity. In this case the cells in question are challenged by both a negative control and the chemotactic factor to see if the differential response is depressed or normal.

Cell orientation in response to a concentration gradient of chemotactic factor can be determined using a Zigmond chamber. A Zigmond chamber is a 2 mm thick microscope slide with two 1 mm deep×4 mm wide grooves ground across the slide, leaving a 1 mm wide unground section between the grooves. Cells are allowed to adhere to a microscope coverglass, which is then inverted so that the cells and some fluid media are positioned over the 1 mm wide unground section of the slide. The coverglass is clamped in this position at each end of the slide, chemotactic factor is pipetted into one of the two grooves, and media is pipetted into the other groove. Capillary action draws the fluid into the grooves. The slide is incubated at 37±1°0C. for about 30 minutes. It is then viewed under a microscope at a magnification of 100 to 1,000 X, and the extent of cell orientation is observed. Migration of the cells can also be studied using elaborate time-lapse image analyzers. Usually, however, the chamber is only used to check the proportion of cells that orient towards a chemotactic factor concentration gradient, compared to the proportion of oriented cells in a control chamber that does not have a chemotactic factor concentration gradient.

Microchemotaxis chambers and some of their applications are described in Falk et al., 37 A 48 Well Micro Chemotaxis Assembly for Rapid and Accurate Measurement of Leukocyte Migration," *Journal of Immunological Methods,* 33, 239–247 (1980); Harvath et al., "Rapid Quantification of Neutrophil Chemotaxis: Use of a Polyvinylpyrrolidone-free Polycarbonate Membrane in a Multiwell Assembly," *Journal of Immunological Methods,* 37, 39–45 (1980); Richards et al., 37 A Modified Microchamber Method for Chemotaxis and Chemokinesis," *Immunological Communications,* 13 (1), 49–62 (1984); Falk et al., "Only the Chemotactic Subpopulation of Human Blood Monocutes Expresses Receptors for the Chemotactic Peptide N-Formylmethionyl-Leucyl-Phenylalanine," *Infection and Immunity,* 36, 450–454 (1982); Zigmond, Sally, Gatewood, Beth and Joe, John, "CD45 is Not Involved in the Processing of Spatial Information Required for Chemotaxis," *Journal of Immunology* (to be published); Zigmond, Sally and Lauffenburger, Douglas A., "Assays of Leukocyte Chemotaxis," *Annual Reviews of Medicine,* 37, 149–155 and Harvath et al., "Two Neutrophil Populations in Human Blood with Different Chemotactic Activities: Separation and Chemoattractant Binding," *Infection and Immunity,* 36 (2), 443–449 (1982), all of which are expressly incorporated by reference herein.

Multiple-site chemotaxis chambers are described in patent application Ser. No. 07/672,561, filed on Mar. 20, 1991, which is expressly incorporated by reference herein.

SUMMARY OF THE INVENTION

The present invention is a single-site or multiple-site chemotaxis test apparatus, often referred to as a chemotaxis chamber. Each site comprises two wells separated by a thin passage. The passage may be 1–25 μm high, 1–10 mm wide and 1 -25 mm long. The optimal dimensions of the passage depend upon the type of cells being studied. The thickness of the passage is selected such that the cells under study cannot flow through the passage, but must "crawl" or "migrate" through the passage under certain conditions. For example, live 10 μm diameter cells in suspension, when encountering a 5 μm high passage, will not flow through this passage under normal conditions, i.e., under no pressure or low pressure. However, the cells will deform and migrate through the passage, adhering to the top and bottom surfaces of the thin passage, under certain conditions. For example, the cells may migrate toward a higher concentration of chemotactic factor. Such mobile adherent cells include many cancer cells, as well as macrophages, monocytes, neutrophils, fibroblasts and endothelial cells.

The present invention can be used to assess chemotactic activity of cells and chemotactic factors, when the cells are restricted to movement in essentially two dimensions by parallel plates. The plates are positioned so close together that they force migrating (mobile) cells to squeeze between them, thus restricting the sites on the cells' surfaces where molecules in the surrounding fluid can contact the cells.

The present invention can be used to study both migration and orientation of adherent mobile cells in a concentration gradient through a thin passage. Cells must deform (flatten out) and migrate ("crawl") through this passage; cells which fail to do this will not appear in the thin passage.

It is a first object of the present invention to provide a simple apparatus and method for the measurement of the activity of cells in response to chemotactic factors.

It is a second object of the present invention to provide a chemotaxis chamber that is inexpensive and disposable.

It is a third object of the present invention to provide a horizontal chemotaxis chamber, i.e., a chemotactic chamber in which the gradient in the concentration of chemotactic factors is perpendicular to the earth's gravitational field.

It is a fourth object of the present invention to provide an apparatus and method for assessing chemotactic activity of cells and chemotactic factors, restricted to essentially two dimensions by two parallel transparent plates.

It is a fifth objective of the present invention to provide an apparatus and method for assessing chemotactic activity of both cells and chemotactic factors involving enhanced microscopic viewing of the activity inside cells during migration by forcing the cells to flatten out between two parallel transparent plates.

It is a sixth object of the present invention to provide a quick and inexpensive method for the analysis of the activity of chemotactic factors.

It is a seventh object of the present invention to provide a quick and inexpensive method for the analysis of the response of various mobile cell populations to concentration gradients of various chemotactic factors.

It is an eighth object of the present invention to provide a chemotaxis chamber comprising two plates bonded to each other with a predetermined gap between the plates.

It is a ninth object of the present invention to provide a chemotaxis chamber comprising two plates bonded to each other, in which a hydrophobic material is disposed between the plates in a pre-determined pattern. The pattern defines the configuration of chemotactic sites, as well as the location of bonding sites for bonding the two plates to each other.

These and other objects of the present invention are achieved as described in the following detailed description of the invention, the appended drawings and the attached claims.

DETAILED DESCRIPTION OF PREFERRED EMBODIMENTS OF THE INVENTION

Figure 1A:
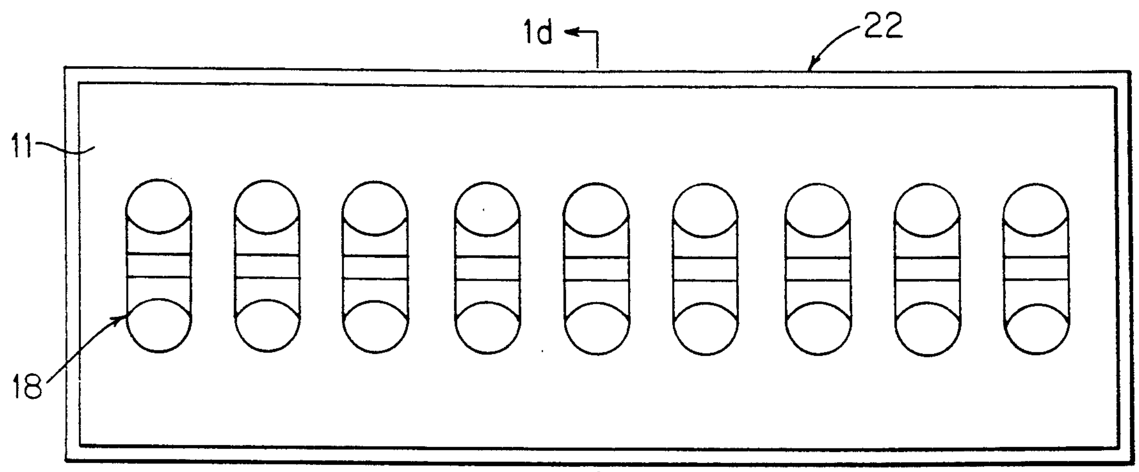
FIG. 1*a* is a top view of the first preferred embodiment of the present invention.
Figure 1B:
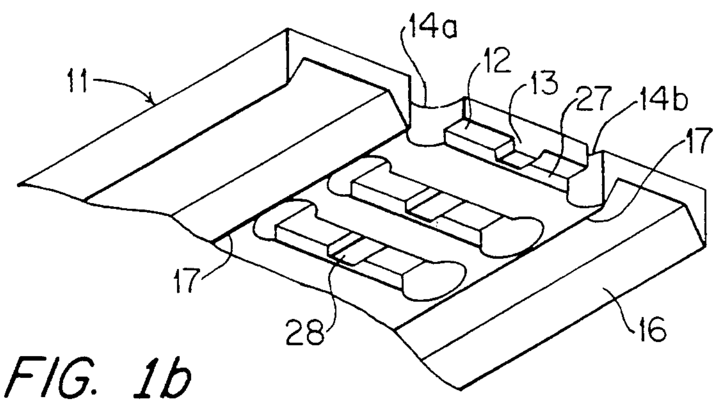
FIG. 1*b* is a perspective cross-sectional view of the top part of the first preferred embodiment of the present invention, taken along A—A of FIG. 1*a*.

The first preferred embodiment of the present invention is a multisite chamber 22 shown in FIG. 1*a*. The multisite chamber 22 is comprised of two major components, a bottom glass plate 10, such as a microscope slide, and a top part 11, preferably made of plastic or glass. As seen in FIG. 1*b*, top part 11 includes protrusion 13 from bottom surface 13, holes 14*a* and 14*b*, knife edges 16 around the periphery of the top part, and knife edges 17 at the bottom of the outer walls that form holes 14*a* and 14*b*. Knife edges 16 and 17 are typically 90° knife edges. Protrusion 13 extends forwards and backwards into side wall 27 and extends down from bottom surface 12 to some point above the bottom edge of side wall 27. The vertical distance between the plane of the bottom surface 28 of protrusion 13 and the horizontal plane extending from the bottom edge of the side wall 27 ranges from 0.1 μm to 25 μm. The bottom points of knife edges 16 and 17 also lie in the same horizontal plane as the points along the bottom edge of the side wall 27.

Figure 1C:
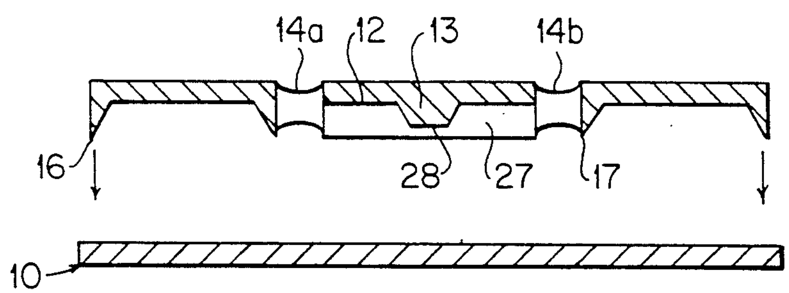
FIG. 1*c* is a cross-sectional view of the first preferred embodiment of the present invention, taken along A—A of FIG. 1*a*, showing how the top part is joined with the bottom plate.
Figure 1D:
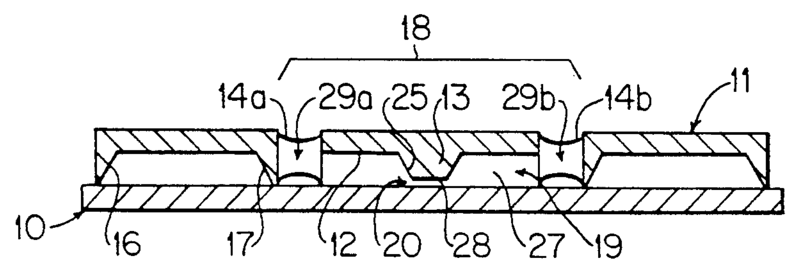
FIG. 1*d* is a cross-sectional view of the first preferred embodiment of the present invention, taken along A—A of FIG. 1*a*, showing the top part assembled to the bottom plate.

As shown in FIG. 1*d*, sites 18 are formed when top part 11 lies atop glass plate 10. Knife edges 16 and 17 are bonded to glass plate 10, as shown in FIGS. 1*c* and 1*d*, using adhesives or other bonding technologies in a conventional manner. As the bottom of knife edges 16 and 17 and the bottom edge of side wall 27 are level with each other, placement of top part 11 on glass plate 10 creates a sealed tunnel-shaped passage 19 with wells 29*a* and 29*b* at each end of the pas extending down from holes 14*a* and 14*b* in the top of the chemotaxis chamber 22. Well 29*a* may be used as the port for a cell suspension, and well 29*b* may be used as the port for a chemotactic factor or control solution. A thin part of passage 19, restricted area 20, is formed by the volume between the bottom surface 28 of protrusion 13 and the top surface of glass plate 10, in the middle of the passage 19. The distance that protrusion 13 extends down from the bottom surface 12 of top part 11 is selected according to the type of study being conducted, as discussed below. Typically, restricted area 20 will be a thinner passage between 0.1 μm and 25 μm high, 0.5–10.0 mm wide, and 0.5–20.0 mm long in the middle of tunnel-shaped passage 19, which joins well 29*a* to the other well 29*b*. In practice, a cell suspension can be inserted through well 29*a* into passage 19 while a chemotactic factor or a control solution can be inserted through well 29*b* into the opposite side of passage 19.

The exact height of restricted area 20 varies with the type of cells being studied. Some cells from the human immune system (e.g., macrophages, monocytes, and neutrophils), require a restricted area between 2 μm and 12 μm high, 4 mm wide and 1 mm long for best results. However, a very thin restricted area of 0.1 μm to 1.0 μm would produce the best results for studying pseudopods of some cancer cell lines, because for those studies the cell bodies themselves must be excluded.

Top part 11 and bottom glass plate 10 are constructed from optical quality transparent materials, so that the cells can be viewed using a microscope with visible or ultraviolet light as they flatten out and migrate through restricted area 20 in passage 19. Restricted area 20 has a flat top and a flat bottom. The cells can be viewed using the microscope from either the top or the bottom side of the chamber, either while they are migrating, or after they have been fixed and stained.

A fluorescent stain or dye can be bound or introduced into the cells being studied. Using ultraviolet light, the number of cells that have migrated from the cell solution side edge 25 of restricted area 20 past a fixed line across restricted area 20 can be counted. Alternatively, the speed the cells move across restricted area 20 can be measured during incubation.

Another way to quantitate the results is to fix and stain the cells after incubation. To do this, the media is first removed by wicking or pipetting it out of site 18 through holes 14*a* and 14*b*. A fixative such as ethanol or methanol is then pipetted into the sites to fix the cells. The fixative is then wicked or pipetted out and a staining solution such as Diff Quick (Scientific Products, McGaw Park, Ill. 60085) is pipetted in. The staining solution is then removed, and the chemotaxis chamber is rinsed out. The cells can then be counted under a microscope, and/or the distance the cells have migrated from the cell solution-side edge 25 of the restricted area 20 can be measured.

Figure 2:
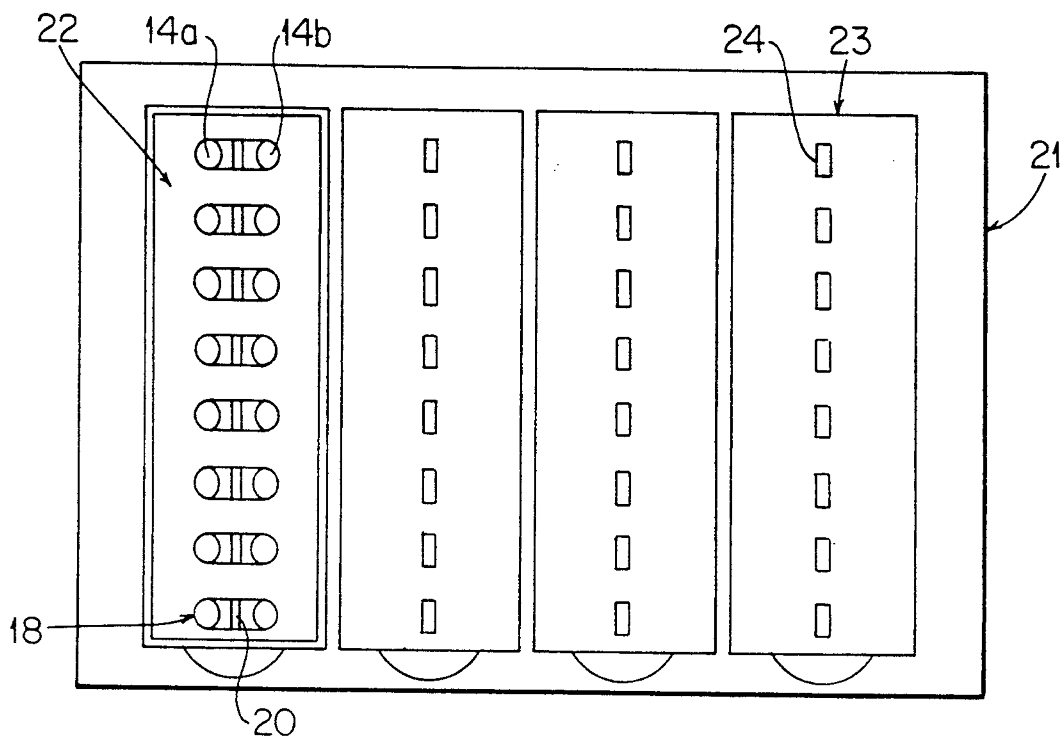
FIG. 2 is a schematic representation of an adapter for holding chemotaxis chambers in an automatic microtiter plate densitometric reader.

Automated densitometric or fluorimetric readings of the restricted area 20 can be executed using an automatic microtiter plate densitometric reader such as Molecular Devices' Uvmax™ or Millipore's Cytofluor™. A special adapter plate 21, shown in FIG. 2, which holds four eight-site chemotaxis chambers 22, is used to adapt the chemotaxis chambers to the automatic microtiter plate densitometric or fluorimetric reader. The outside dimensions of the adapter plate 21 fit into the automatic microtiter plate reader. In the middle of each of the four recesses 23 which hold the eight site chemotaxis test apparatus 22 are eight slots 24 between 0.5 and 3 mm wide and between 1 and 4 mm long. These slots allow light to penetrate the otherwise opaque plate 21.

Slots 24 line up with the restricted area 20 of each passage 19 of each chemotactic site 18. Upon irradiation with light, a densitometer or a fluorimeter detects the amount of light transmitted through or emitted from restricted area 20. The amount of light transmitted or emitted will vary with the number of cells that have moved into restricted area 20.

Figure 3A:
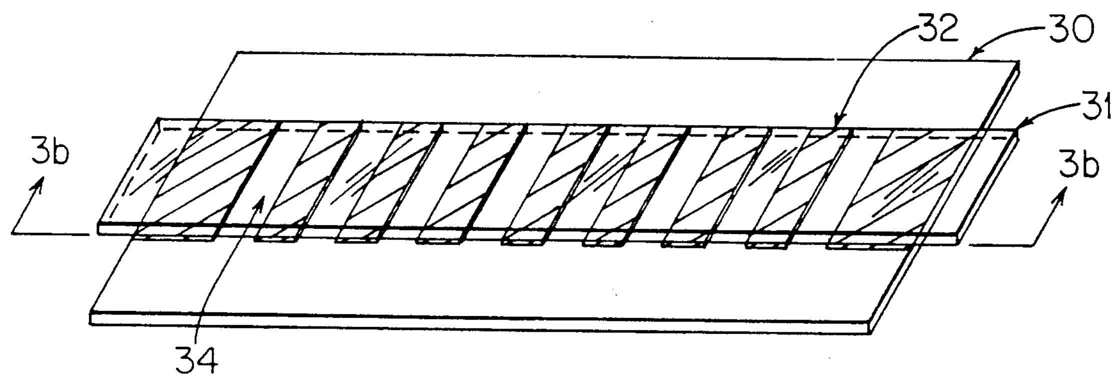
FIG. 3*a* is a top perspective view of a second preferred embodiment of the present invention.
Figure 3B:
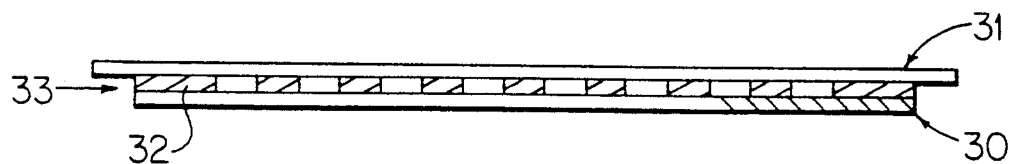
FIG. 3*b* is a cross-sectional view of the second preferred embodiment of the present invention, taken along B—B of the FIG. 3*a*.
Figure 3C:
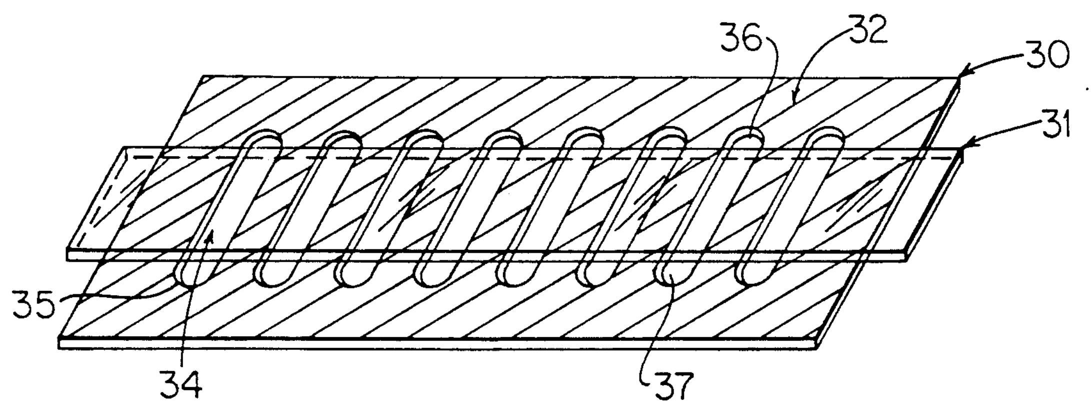
FIG. 3*c* is a top perspective view of the second preferred embodiment of the present invention with additional areas of hydrophobic coating.

A second preferred embodiment of the present invention is shown in FIGS. 3*a*, 3*b*, and 3*c*. The chemotaxis chamber shown in FIG. 3*a* comprises a transparent flat glass or plastic bottom plate 30 with a transparent glass or plastic top plate 31 affixed to the top of bottom plate 30, leaving a gap of 0.1–25 μm between the two plates.

Between the top and bottom plates are areas of hydrophobic material 32 adhering to the top surface of the bottom plate 30. The areas of hydrophobic material 32 are approximately the thickness of the desired 0.1–25 μm gap 33 between the two plates, as shown in FIG. 3*b*. The hydrophobic material can be vapor-deposited, printed, rolled, sprayed, or sputtered onto the surface of the bottom plate 30. The areas of hydrophobic material are deposited on the bottom plate in such a manner as to create a pattern whereby rectangular areas of the hydrophobic material alternate with rectangular areas where no hydrophobic material has been deposited. Additionally, the areas of hydrophobic material are long enough to span the entire width of the top plate 31. The top plate is affixed to the top surface of the areas of hydrophobic coating attached to the bottom plate, using a bonding technique such as ultrasonic welding, if both components are plastic (e.g., polystyrene); gluing; or using other appropriate adhesives if both components are glass; heat sealing; and solvent bonding. If a bonding agent is used, it is applied to top surface of the hydrophobic material and bonds to the bottom surface of the top plate 31.

The gap between the two plates must be carefully maintained during bonding. After bonding, the gap size is measured with the aid of a microscope. The instruments are then sorted into different groups according to the size of their gaps.

One technique for obtaining a specific gap size is to deposit a uniform thickness of material on the bottom or top plate equal to the thickness of the desired gap before bonding the two plates together. A second technique is to machine impress or mold the depressions in the top or bottom plates before bonding them together. A third technique is to use an adhesive which can be applied in thin lines across the top or bottom plate such that the capillary action of the fluid adhesive between the two plates under a given amount of pressure applied to the two plates produces the desired gap.

The third technique for implementing the second preferred embodiment of the present invention can be applied using UV activated polyurethane adhesives with low viscosity, a fixture which can measure the size of the gap, and a system for controlling the pressure applied between the plates. When a gap with the desired size is obtained, the polyurethane adhesive is activated with UV light, and the two plates are bonded to each other.

Once the two plates are joined together, rectangular chemotactic sites 34 are created between each area of hydrophobic coating. Thus, a drop of cell solution can be placed at one end of the site where the gap between the top and bottom plates begins, while a drop of a chemotactic factor or control solution can be placed at the other end of the site where the gap begins. The chemotactic effects can then be studied as a concentration gradient is formed between the solutions from opposite ends of site 18.

Alternatively, the areas of hydrophobic coating can extend out from under the top plate to cover the rest of the surface of the bottom plate except for semi-circular areas 36 and 37 at the ends of each site. This is shown in FIG. 3*c*.

Figure 4A:
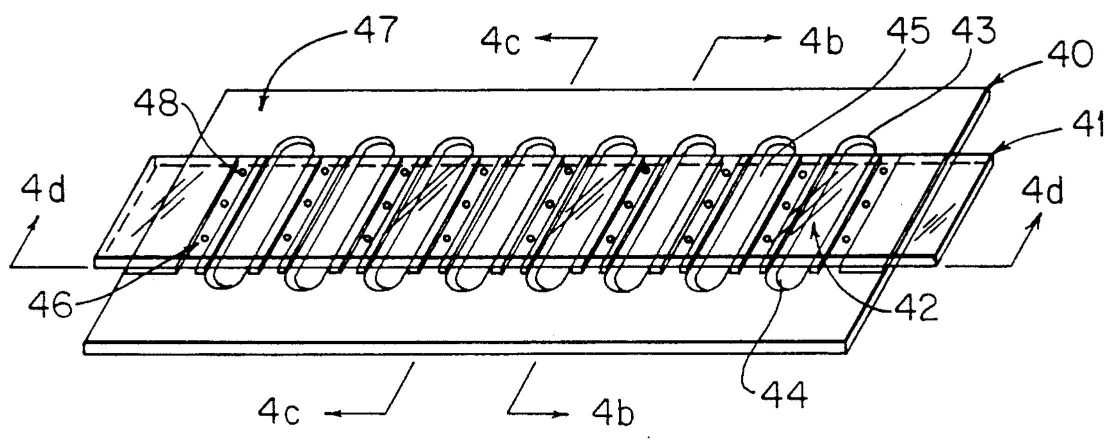
FIG. 4*a* is a top perspective view of a third preferred embodiment of the present invention.
Figure 4B:
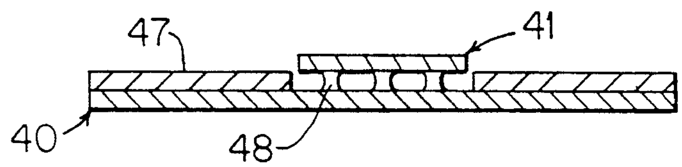
FIG. 4*b* is a cross-sectional view of the third preferred embodiment of the present invention, taken along C—C of FIG. 4*a*.
Figure 4C:
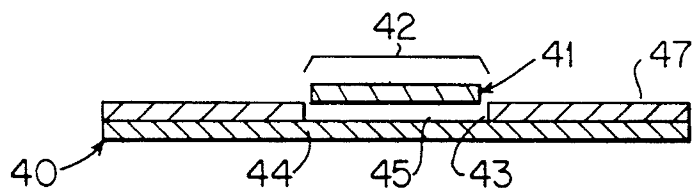
FIG. 4*c* is a cross-sectional view of the third preferred embodiment of the present invention, taken along D—D of FIG. 4*a*.

A third preferred embodiment is shown in FIG. 4*a*, 4*b*, 4*c*, and 4*d*. It is similar to the second preferred embodiment, as top plate 41 is held away from contact with bottom plate 40 by a hydrophobic material 47 adhering to bottom plate 40 which is approximately the thickness of the desired 0.1–25 μm gap between the two plates. However, this material, which can be vapor-deposited, printed, rolled, sprayed, or sputtered onto bottom plate 40, is applied in an alternating pattern leaving two kinds of areas free of hydrophobic coating. The first kind of hydrophobic-free area forms a number of chemotaxis test sites 42 when the top plate 41 is affixed to the bottom plate 40. As shown in FIGS. 4*a* and 4*c*, each chemotaxis test site 42 spans the width of the top plate 41 and extends on either side to form semi-circular ends 43 and 44 free of hydrophobic material. Thus, a drop of cell solution can be placed at one end of the site where the gap between the top and bottom plates begins, while a drop of a chemotactic factor or control solution can be at the other end of the site where the gap begins. The chemotactic effects can then be studied as the solutions from opposite ends of the site form a concentration mix.

FIG. 4*a* shows eight such openings, 9 mm on center. Each chemotaxis test site 42 has a semi-circular top section 43, a semi-circular bottom section 44, and a rectangular center section 45. The optimal size of these chemotaxis test sites 42 varies with the application. Typical sites are 0.5–6 mm wide by 5–20 mm long.

Figure 4D:
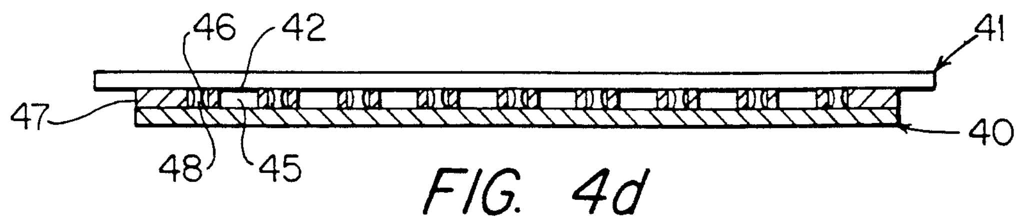
FIG. 4*d* is a cross-sectional view of the third preferred embodiment of the present invention, taken along E—E of FIG. 4*a*.

The second kind of hydrophobic-free area defines the location where the adhesive for bonding the plates together is located. These adhesive sites 46 are rectangular, span the width of the top plate, and lie between the chemotaxis test sites 42. Each adhesive site 46 is bounded on each side by hydrophobic material 47. Drops of an appropriate adhesive 48 are deposited within each adhesive site 46. As shown in FIG. 4*b*, the adhesive 48 bonds the top plate 41 to the bottom plate 40 at the gap determined by the height of the areas of hydrophobic material 47. FIG. 4*d* shows how the adhesive sites 46 and the chemotaxis sites 42 alternate, each separated from the other by an area of hydrophobic material 47.

The material 47 bonded to bottom plate 40 is hydrophobic and prevents fluids (cells suspended in media, chemotactic factor solutions, or control solutions) pipetted into the ends of the chemotaxis test sites 42 from wicking across to an adjacent chemotaxis test site 42. The fluid is restricted to filling the gap between the two plates, but air can escape between top plate 41 and hydrophobic material 47. This prevents bubble entrapment in rectangular center section 45.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A chemotactic test apparatus comprising:

(a) a bottom plate having a top surface; and (b) a top plate, said top plate having:

(i) a peripheral knife-edge protrusion around the periphery of the top plate, said peripheral knife-edge protrusion having a first height;

(ii) at least one pair of holes;

(iii) hole-pair knife-edge protrusions around the outer periphery of each pair of holes, the height of said hole-pair knife-edge protrusions substantially matching the height of the peripheral knife-edge protrusion;

(iv) a substantially flat-bottomed protrusion in between the two holes in each pair of holes, the height of said flat-bottomed protrusion being less than the height of said peripheral knife-edge protrusion; and (v) front and rear hole-pair side walls extending down from the bottom surface of the top plate and joining the pair of holes, into which the flat-bottomed protrusion extends forwards and backwards, the height of said hole-pair side walls substantially matching the height of the peripheral knife-edge protrusions, wherein the top plate is attached to the top surface of the bottom plate such that the peripheral knife-edge protrusions form a seal around the periphery of the assembly, the hole-pair knife edges and the front and rear hole-pair side walls form a seal around the periphery of each pair of holes, thus forming a chemotactic site, each site having a pair of wells formed by the holes in the top plate, and also having a passageway between each pair of wells, each said passageway having a restricted area formed by the volume between the top surface of the bottom plate, the front and rear walls of the hole-pair side walls, and the bottom surface of the flat-bottomed protrusion, such that the height of the restricted area is less than the diameter of typical cells to be tested.

2. The chemotactic test apparatus of claim 1, wherein the restricted area in the passageway between each pair of holes is 2 μm–12 μm high.

3. The chemotactic apparatus of claim 1, wherein the restricted area in the passageway between each pair of holes is 0.1 μm–25 μm high.

4. The chemotactic apparatus of claim 3, wherein the restricted area in the passageway between each pair of holes is 0.5 mm–10 mm wide and 0.5 mm to 20 mm long.

5. The chemotactic apparatus of claim 1, wherein the top plate and the bottom plate are constructed of transparent materials.

6. The chemotactic apparatus of claim 1, further comprising a cell suspension in one well of a first pair of wells and a chemotactic factor placed in the other well of the first pair of wells.

7. The chemotactic apparatus of claim 6, further comprising a cell suspension in one well of a second pair of wells and a control solution in the other well of the second pair of wells.

8. A chemotactic apparatus comprising:

(a) a transparent flat top plate having a first width;

(b) a transparent flat bottom plate having a second width, wherein the second width is greater than the first width; and (c) a coating of uniformly thick hydrophobic material between said bottom plate and said top plate, said coating extending at least the width of the top plate and having a plurality of rectangular openings therein extending at least the width of the top plate, each of said rectangular openings forming a chemotactic site, such that the hydrophobic material forms a gap between the bottom of the transparent flat top plate and the top of the transparent flat bottom plate is less than the diameter of the cells to be tested.

9. The chemotactic apparatus of claim 8, wherein the hydrophobic coating is attached to the bottom plate and to the top plate.

10. The chemotactic apparatus of claim 9, further comprising a cell suspension and a chemotactic factor in the chemotactic site.

11. The chemotactic apparatus of claim 9, wherein the hydrophobic coating has a uniform thickness of 0.1–25 μm.

12. The chemotactic apparatus of claim 8, wherein the hydrophobic coating extends to cover the surface of said bottom plate not underlying said top plate, said hydrophobic coating not covering semicircular areas at the ends of each of said rectangular openings forming a chemotactic site.

13. The chemotactic apparatus of claim 8, wherein the coating includes a second plurality of openings of a second kind in addition to the rectangular openings forming the chemotactic test site, wherein adhesives in said openings of the second kind bond the top plate to the bottom plate, the size of the gap between the top plate and the bottom plate being determined by the thickness of the hydrophobic coating.

14. The chemotactic apparatus of claim 13, wherein the hydrophobic coating extends to cover the surface of said bottom plate not underlying said top plate, said hydrophobic coating not covering semicircular areas at the ends of each of said rectangular openings forming a chemotactic site.

15. The chemotactic apparatus of claim 13, wherein the hydrophobic coating has a uniform thickness of 0.1–25 μm.

16. A method for performing chemotactic tests using a chemotactic test apparatus comprising a bottom plate having a top surface and a top plate, said top plate having a peripheral knife-edge protrusion around the periphery of the top plate, at least one pair of holes, hole-pair knife-edge protrusions around the periphery of each pair of holes, a substantially flat-bottomed protrusion in between the two holes, and front and rear hole-pair side walls joining each pair of holes into which the flat-bottomed protrusion extends forwards and backwards, the height of said flat-bottomed protrusion being less than the height of said peripheral knife-edge protrusion and said front and rear hole-pair side walls, comprising:

(a) assembling the top plate and the bottom plate such that the peripheral knife-edge protrusions form a seal around the periphery of the assembly, the hole-pair knife edges and the front and rear hole-pair side walls form a seal around the periphery of each pair of holes, thus forming a chemotactic site, each site having a pair of wells formed by the holes in the top plate, and also having a passageway between each pair of wells, each said passageway having a restricted area formed by the volume between the top surface of the bottom plate, the front and rear walls of the hole-pair side walls, and the bottom surface of the flat-bottomed protrusion;

(b) placing a cell suspension in a first one of a pair of wells of a first chemotactic site;

(c) placing a chemotactic factor in the second one of said pair of wells of the first chemotactic site;

(d) incubating the chemotactic test apparatus for a pre-determined time period;

(e) fixing the cells; and (f) counting the number of cells that have migrated into the second well, wherein the height of said passageway is smaller than the diameter of the cells.

17. The method of performing chemotactic tests of claim 16, further comprising:

(g) placing a cell suspension in a first one of a pair of wells of a second chemotactic site;

(h) placing a control solution in the second one of said pair of wells of a second chemotactic site; and (j) comparing the chemotactic activity of the cell suspension at the first chemotactic site to the chemotactic activity of the cell suspension at the second chemotactic site.

18. The method of performing chemotactic tests of claim 16, further comprising measuring the distance the cells having migrated.

19. The method of performing chemotactic tests of claim 16, wherein the restricted area in the passageway between each pair of holes is 0.1 μm–25 μm high.

20. The chemotactic method of claim 16, wherein the restricted area in the passageway between each pair of holes is 0.5 mm–10 mm wide and 0.5 mm to 20 mm long.

21. The chemotactic method of claim 16, wherein the top plate and the bottom plate are constructed of transparent materials.

22. The chemotactic method of claim 16, wherein the hydrophobic coating extends to cover the surface of said bottom plate not underlying said top plate, said hydrophobic coating not covering semicircular areas at the ends of each of said rectangular openings forming a chemotactic site.

23. A method for performing chemotactic tests using a chemotactic test apparatus comprising a transparent flat top plate having a first width, a transparent flat bottom plate having a second width, wherein the second width is greater than the first width, and a coating of uniformly thick hydrophobic material between said bottom plate and said top plate, said coating extending at least the width of the top plate and having a plurality of rectangular openings therein extending at least the width of the top plate, each of said rectangular openings forming a chemotactic site having a first end and a second end, comprising:

(a) placing a cell suspension at the first end of a first chemotactic site;

(b) placing a chemotactic factor at the second end of the first chemotactic site;

(c) incubating the chemotactic test apparatus for a pre-determined time period;

(d) fixing the cells; and (e) counting the number of cells that have migrated from the first end of the first chemotactic site past a line perpendicular to a line drawn from the first end of the chemotactic site to the second end of the chemotactic site within the restricted area, wherein the hydrophobic material forms a gap between the bottom of the transparent flat top plate and the top of the transparent flat bottom plate is less than the diameter of the cells.

24. The method of performing chemotactic tests of claim 23, further comprising:

(f) placing a cell suspension in the first end of a second chemotactic site;

(g) placing a control solution in the second end of a second chemotactic site;

(h) and comparing the chemotactic activity of the cells suspension at the first chemotactic site to the chemotactic activity of the cell suspension at the second chemotactic site.

25. The method of performing chemotactic tests of claim 23, further comprising measuring the distance the cells having migrated.

26. The method of performing chemotactic tests of claim 23, wherein the hydrophobic coating is 0.1 μm–25 μm high.

27. The chemotactic method of claim 23, wherein the hydrophobic coating extends to cover the surface of said bottom plate not underlying said top plate, said hydrophobic coating not covering semicircular areas at the ends of each of said rectangular openings forming a chemotactic site.

28. The method of performing chemotactic tests of claim 23 wherein the hydrophobic coating includes a second plurality of openings of a second kind in addition to the rectangular openings forming the chemotactic test sites, wherein adhesives in said openings of the second kind bond the top plate to the bottom plate, the size of the gap between the top plate and the bottom plate being determined by the thickness of the hydrophobic coating.

29. The chemotactic method of claim 28, wherein the hydrophobic coating extends to cover the surface of said bottom plate not underlying said top plate, said hydrophobic coating not covering semicircular areas at the ends of each of said rectangular openings forming a chemotactic site.

30. A method for measuring the chemotactic activity of cells from an immune system comprising:

(a) providing a chemotactic test apparatus having:

(i) a transparent top plate, the top plate having at least one pair of holes, a knife-edge protrusion around each pair of holes, a flat-bottomed protrusion between the holes in each pair of holes, and front and rear hole-pair side walls joining each pair of holes into which the flat-bottomed protrusion extends forwards and backwards; and (ii) a transparent bottom plate, the top surface of the bottom plate being attached to the bottom surface of the top plate such that the hole-pair knife edge protrusions around each pair of holes and the bottom edges of the front and rear hole-pair side walls seal against the top surface of the bottom plate, forming chemotactic test sites having two wells, each well being formed by one of the holes in the pair of holes, and a passageway between the holes, said passageway having a restricted area formed by the bottom surface of the flat-bottomed protrusion and the top surface of the bottom plate;

(b) placing a cell suspension in a first well of a first chemotactic test site;

(c) placing a chemotactic factor in the second well of the first chemotactic test site;

(d) incubating the chemotactic test apparatus for a predetermined time period;

(e) fixing the cells; and (f) counting the cells that having migrated from the first well past a line perpendicular to a line drawn from the first well to the second well within the restricted area, wherein the height of said passageway is less than the diameter of the cell.

31. The method for measuring the chemotactic activity of cells from an immune system of claim 30, further comprising:

(g) placing a cell suspension in a first well of a second chemotactic test site;

(h) placing a control solution in the second well of the second chemotactic test site; and (i) comparing the chemotactic activity of the cell suspension at the first chemotactic test site to the chemotactic activity of the cell suspension at the second chemotactic test site.

32. The method of claim 31, wherein the restricted area in the passageway is between 2 μm and 12 μm high.

* * * * *